United States Patent [19]

Smith

[11] Patent Number: 4,806,338

[45] Date of Patent: Feb. 21, 1989

[54] ANTIPERSPIRANT AEROSOL COMPOSITIONS

[75] Inventor: Scott E. Smith, Cincinnati, Ohio

[73] Assignee: The Procter & Gamble Company, Cincinnati, Ohio

[21] Appl. No.: 826,409

[22] Filed: Feb. 5, 1986

Related U.S. Application Data

[63] Continuation-in-part of Ser. No. 739,248, May 30, 1985, abandoned.

[51] Int. Cl.⁴ .................. A61K 7/34; A61K 7/36; A61K 7/38; A61K 9/12
[52] U.S. Cl. .......................... 424/47; 424/66; 424/67; 424/68
[58] Field of Search .................. 424/65, 66, 67, 68, 424/47

[56] References Cited

U.S. PATENT DOCUMENTS 4,268,499 5/1981 Keil ........................................ 424/65
4,280,994 7/1981 Turney .................................. 424/65

FOREIGN PATENT DOCUMENTS 2096891 10/1982 United Kingdom ................. 424/68

Primary Examiner—Dale R. Ore
Attorney, Agent, or Firm—David L. Suter; Steven J. Goldstein; Douglas C. Mohl

[57] ABSTRACT

Antiperspirant aerosol compositions comprising from about 1% to about 40% of a particulate antiperspirant material, from about 0.005% to about 6.0% of a functionalized siloxane and from about 60% to about 95% of an aerosol propellant. Preferably the functionalized siloxane is an amino-functional silicone. Also preferably, the compositions also contain a silicon gum material and a volatile silicone oil.

14 Claims, No Drawings

ANTIPERSPIRANT AEROSOL COMPOSITIONS

This application is a continuation-in-part of Application Ser. No. 739,248, filed May 30, 1985, now abandoned.

BACKGROUND OF THE INVENTION

The present invention relates to antiperspirant compositions for administration as an aerosol to human skin. More particularly, it relates to such aerosol compositions with improved cosmetic characteristics.

Compositions designed to stop or reduce the flow of human perspiration are well known in the chemical and cosmetic literature. Such antiperspirant compositions may be applied to the skin by a variety of methods. For example, S. Plechner, "Antiperspirants and Deodorants" 2 *Cosmetics, Science and Technology*, 373–416 (M. Balsam and E. Sagarin ed. 1972), describes antiperspirant compositions in spray, roll-on, cream and stick forms. Depending upon such factors as the method of application, the intended use, and the desired rheology, such compositions may contain a variety of different vehicle materials in addition to an astringent antiperspirant active.

For a variety of reasons, one method of application that has gained wide consumer acceptance is the aerosol form. Such compositions typically are anhydrous systems comprising an antiperspirant salt dispersed in a liquid vehicle together with a liquified volatile propellant in a pressurized aerosol container. The aerosol spray is created, then, by the rapid boiling of the propellant upon dispensing from an atomizing valve. Such aerosol containers are described, for example, in U.S. Pat. No. 3,083,917 and U.S. Pat. No. 3,083,918, Abplanalp, et al., issued Apr. 2, 1963, and U.S. Pat. No. 3,544,258, Presant, et al., issued Dec. 1, 1970.

Antiperspirant aerosol compositions present, however, several cosmetic problems. For example, such compositions may create a cooling sensation when applied to the skin, or they may be very dusty or powdery once applied. such compositions may also create excessive dustiness or mistiness during application. Also, such compositions may require excessive shaking or agitation prior to, and during, use in order to maintain adequate suspension or dispersion of the active material in the product. Failure to maintain such active or product suspension may lead (for example) to dispensing of propellant or other vehicle materials with little or no antiperspirant active. This problem may be particularly significant with respect by compositions containing high molecular weight silicone gums, as disclosed in U.S. Pat. No. 4,152,416, Spitzer, et al., issued May 1, 1979.

It has now been discovered that aerosol antiperspirant compositions containing certain functionalized siloxanes have improved application, cosmetic and performance characteristics than compositions known in the art. For example, the aerosol antiperspirants of this invention have improved adherence to the skin, and improved product suspension and redispersibility (i.e., maintaining more extensive suspension or dispersion of active materials in the product, with lower rates of settling), as well as other improved cosmetic characteristics.

SUMMARY OF INVENTION

The present invention provides aerosol antiperspirant compositions comprising:
(a) from about 1% to about 40% of a particulate antiperspirant material;
(b) from about 0.005% to about 6.08% of a functionalized siloxane; and
(c) from about 60% to about 95% of an aerosol propellant.

Preferably, the functionalized siloxane is an amino-functional silicone. Also preferably these compositions also contain from about 0.05% to about 5.0% of a silicone gum material.

DESCRIPTION OF THE INVENTION

The aerosol antiperspirant compositions of the present invention contain three essential ingredients: particulate antiperspirant materials, a functionalized siloxane, and an aerosol propellant. These compositions (herein "antiperspirant aerosols") encompass any such composition intended to apply antiperspirant material to human skin by means of a suspension of fine particulates or droplets in a propellant gas. Thus, these compositions are, in general, dispensed from a conventional aerosol container.

Specifically, the compositions of the present invention comprise:
(a) from about 1% to about 40% of a particulate antiperspirant material;
(b) from about 0.005% to about 6.0% of a functionalized siloxane; and
(c) from about 60% to about 95% of an aerosol propellant.

(All percentages herein are by weight of total composition.) Preferably the antiperspirant materials are present at a level of from about 3% to about 24%, more preferably from about 5% to about 12%. Also, preferably, the functionalized siloxane is present at a level of from about 0.005% to about 4.0%, more preferably from about 0.005% to about 2.0%, and more preferably from about 0.005% to about 0.1%. The compositions of the present invention may, in addition, contain certain optional components which may vary the efficacy and/or the physical characteristics of the composition. The essential and optional ingredients used in the present invention must be "cosmetically-acceptable", i.e., safe for human use and asethetically acceptable at the levels at which such materials are used in the present compositions, at a reasonable risk/benefit ratio.

Particulate Antiperspirant Materials

The particulate antiperspirant materials of this invention comprise any compound or composition having antiperspirant activity. Astringent metallic salts are preferred antiperspirant materials for use herein, particularly including the inorganic and organic salts of aluminum, zirconium and zinc, and mixtures thereof. Particularly preferred are the aluminum and zirconium salts such as aluminum halides, aluminum hydroxide halides, zirconyl oxide halides, zirconyl hydroxy halides, and mixtures thereof.

Preferred aluminum slats include those of the formula $Al_2(OH)_aCl_b \cdot xH_2O$ wherein a is from about 2 to about 5; a+b=6; x is from about 1 to about 6; and wherein a, b, and x may have non-integer values. Particularly preferred are aluminum chlorhydroxides referred to as "5/6 basic chlorhydroxide", wherein a=5, and "⅔ basic chlorhydroxide," wherein a=4. Processes for preparing aluminum salts are disclosed in the following documents, all incorporated by reference herein: U.S. Pat. No. 3,887,692, Gilman, issued June 3, 1975; U.S. Pat. No. 3,904,741, Jones et al., issued Sept. 9, 1975; U.S. Pat. No. 4,147,766, Kozischek, issued Apr. 3, 1979; U.S. Pat. No. 4,359,456, Gosling, et al., issued Nov. 19, 1982; and British Patent Specification No. 2,048,229, Fitzerald, et al., published Dec. 10, 1980. Mixtures of aluminum salts are described in British Patent Specification No. 1,347,950, Shin, et al., published Feb. 27, 1974 (incorporated by reference herein).

Zirconium salts are also preferred for use in antiperspirant sticks of the present invention. Such salts are of the general formula

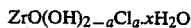

wherein a is from about 1.5 to bout 1.87; x is from about 1 to about 7; and wherein a and x may have non-integer values. These zirconium salts are disclosed in Belgium Pat. No. 825,146, Schmitz, issued Aug. 4, 1975, (incorporated by reference herein). Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in the following patent documents, all incorporated by reference herein: U.S. Pat. No. 3,679,068, Luedders, et al., issued Feb. 12, 1974; U.S. Pat. No. 4,120,948, Shelton, issued Oct. 17, 1978; and U.K. patent application No. 2,144,992, Callaghan, et al., published Mar. 20, 1985.

Functionalized Siloxane

The aerosol antiperspirants of the present invention contain one or more derivatized polydimethyl siloxanes, herein referred to as "functionalized siloxanes", wherein said siloxanes contain electronegative functional groups. Functionalized siloxanes, among those useful herein, include those of the following formula:

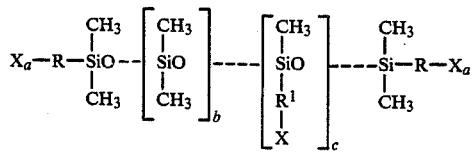

wherein a is 0 or 1, b is from about 50 to about 2,000, and c is from about 0 to about 300; x is Cl, F, —COOH, or —N(R$^3$)$_2$; R is CH$_3$ (if a =0) or R$^1$ (if a=1); R$^1$ is straight or branched alkyl containing from 1 to 10 carbon atoms; R$^2$ is H or R$^1$; R$^3$ is R$^2$ or R$^1$N(R$^2$)$_2$; and wherein a+c>0 and the ratio of (a+c)/(b+c) is from about 0.01 to about 0.30. It is understood that, in the above formula, the substituted "c" siloxane units may be interspersed with the unsubstituted "b" siloxane units. In preferred functionalized siloxanes of the above formula, b is from about 200 to about 1200, c is from about 2 to about 200, and the ratio of (a+c)/(b+c) is from about 0.01 to about 0.15. Particularly preferred functionalized siloxanes are diamine substituted, wherein X is NR$^2$(R$^1$N(R$^2$)$_2$).

Molecular weights of preferred functionalized siloxanes useful herein, as determined by gel permeation chromatography/low angle laser light scattering (GPC/LALLS), are from about 2,000 to about 150,000, preferably from about 20,000 to about 150,000, more preferably from about 50,000 to about 150,000. For preferred amino-functional sillicones, the ratio (a+c)/(b+c) of the above formula, manifested as milliequivalents of amine per gram (meq/g) of silicone polymer, preferably is from about 0.01 to about 1.5 meq/g, more preferably from about 0.01 to about 0.7 meq/g.

Among the amino-functional silicones useful herein are the following commercially-available materials: Q2-8075 and X2-8107, manufactured by Dow Corning Corporation; Y-7717 and Y-12035, manufactured by Union Carbide Corporation; 756, 784, and 801, manufactured by SWS Silicones Corporation; GE 176-10977 and GE 179-10979, manufactured by General Electric Company; and 2181 manufactured by Petratch Systems, Inc. Dow Corning Y-12035, GE 176-10977, and SWS 801 are particularly preferred amino-functional silicone materials useful herein. Among the other commercially-available functionalized (non-amino) siloxanes useful herein are PS402 carboxy-substituted siloxane and PS183 trifluoro-substituted siloxane (manufactured by Petrarch Systems, Inc.).

Aerosol Propellant

The present composition contains one or more volatile materials, herein "aerosol propellants", which in a gaseous state, carry the other components of the present invention in particulate or droplet form. The aerosol propellants useful in the present invention typically have a boiling point within the range of from about −45° C. to about 5° C. The aerosol propellants are liquified when packaged in conventional aerosol containers under pressure. The rapid boilding of the aerosol propellant upon leaving the aerosol container aids in the atomization of the other components of the present invention.

Aerosol propellants useful in the present invention include those well known in the art. Such aerosol propellants include the chemically-inert hydrocarbons such as propane, n-butane, isobutane and cyclopropane, and mixtures thereof, as well as halogenaed hydrocarbons such as dichlorodiluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), and monochlorodifluoromethane, and mixtures thereof. Isobutane, used singly or admixed with other hydrocarbons, is preferred for use in the present aerosol antiperspirants.

Optional Components

The compositions of the present invention may also contain optional components which modify the physical characteristics of the composition or serve as "active" components when deposited on the skin in addition to the particulate antiperspirant material. Additional active components include bacteristats and fungistats. Non-active components useful herein may include, for example, bulking agents, solvents, emollients, colorants, and perfumes. Perfumes are typically incorporated at levels of from about 0.001% to about 0.5%. Optional components useful herein are described in the following patent documents, all incorporated by reference herein: British patent application No. 2,072,503, Geary, published Oct. 7, 1981; European Pat. No. 28,853, Beckmeyer, et al., issued July 11, 1984, and U.S. Pat. No. 4,152,416, Spitzer, et al., issused May 1, 1979. It should be noted that certain functionalized siloxanes of this invention, when used at the higher levels disclosed herein, may produce undesirable effects on the fragrance of certain optional perfume materials. Such interaction could necessitate use of lower levels of functionalized siloxane and/or use of alternative perfume materials.

A particularly preferred optional material for use in the present compositions is a silicone gum. As referred to herein, "silicon gum" materials useful in the present compositions are those non-functionalized siloxanes having a viscosity of from about 500,000 to about 100,000,000 centistokes at 25° C. These materials are incorporated in the present compositions at a level of from about 0.05% to about 5.0%, preferably from about 0.10% to about 2.0%. Preferred silicone gums include linear and branched polydimethyl siloxanes, of the following general formula:

wherein n is from about 2,000 to about 15,000, preferably from about 2,000 to about 7,000. The silicone gums useful herein may also be substituted with non-electronegative substituents. Silicone gums among those useful herein are available from a variety of commercial sources, including X2-1346 and Dow Corning 200 Fluid (manufactured by Dow Corning Corporation) PS240 (manufactured by Petrarch Systems, Inc.). and SE76, SE30 and SE32 Silicone Gums (manufactured by General Electric Company).

The present compositions also preferably contain an additional solvent material, particularly when the silicone gums described above are also used. Suitable solvents include pentane, hexane, trichloro trifluoroethylene, trichloro fluoromethane, dichloro fluoromethane, methylene chloride, and volatile and non-volatile non-functoinalized silicone oils.

Volatile silicone oils are preferred solvent materials useful in the present aerosol compositions at levels of from about 0.05% to about 15.0%, preferably from about 1.0% to about 6.0%. (As used herein, "volatile" refers to thosee materials which have a measurable vapor pressure at ambient conditions.) Such volatile silicone oils may be cyclic or linear. A description of various volatile silicone oils is found in Todd, et al., "Volatile Silicone Fluids for Cosmetics", 91 *Cosmetics and Toiletries*, 27–32 (1976), incorporated by reference herein. Linear volatile silicones generally have viscosities of less than about 5 centistokes at 25° C., whereas the cyclic silicones have viscosities of less than about 10 centistokes. Examples of volatile silicone oils useful in the present invention include: Dow Corning 344 and Dow Corning 345 (sold by Dow Corning Corporation); 7207 and 7158 (sold by General Electric Company); and SWS-03314 (sold by SWS Silicones Corporation).

The present compositions may also contain a bulking or suspending agent, at levels of from about 0.1% to about 7%, preferably from about 0.4% to about 3.5%. (However, preferred compositions of the present invention do not require the presence of a bulking or suspending agent.) Such bulking/suspending agents include talc, colloidal silicas, clays and mixtures thereof. Clays and colloidal silicas are particularly preferred. Clay bulking/suspending agents include montmorillonite clays and hydrophobically treated montmorillonites, e.g., bentonites, hectorites and colloidal magnesium aluminum silicates. These materials are available from a variety of sources, including Laponite hectorite (sold by Laponite Industries, Ltd.) and Veegum magnesium aluminum silicate (sold by R. T. Vanderbilt Co.). A preferred clay bulking/suspending agent is hydrophobically-treated montmorillonite, such as the Bentone bentonites (sold by NL Industries, Inc.). Colloidal silicas are also readily available, such as Cab-O-Sil pyrogenic colloidal silica (sold by Cabot Corporation).

Methods

The present invention encompasses methods of preparing aerosol antiperspirant compositions having improved application and cosmetic characteristics. These compositions can be made by a variety of well established methods known in the art. Preferred methods of making compositions of this invention which include silicone gum materials, involve mixing the silicone gum materials with a solvent, such as a volatile silicone oil, prior to mixture with the other components of the invention.

The following non-limiting examples illustrate the compositions, processes and uses of the present invention.

EXAMPLE I

An aerosol antiperspirant composition of the present invention is made comprising:

| Component | % by weight |
|---|---|
| Reheis Macrospherical - 95[1] | 12.00 |
| SE76 Silicone gum[2] | 0.58 |
| SWS 801[3] | 1.00 |
| cyclomethicone (D-5)[4] | 3.40 |
| propellant A-46[5] | 83.02 |

[1]5/6 aluminum chlorhydrate antiperspirant active, sold by Reheis Chemical Company
[2]high molecular weight silicone gum, with a viscosity of approximately 15 × 10$^6$ centipoise, sold by General Electric Company, purchased as a pre-mix of 15% gum and 85% cyclomethicone
[3]diamino-functional silicone, of molecular weight of approximately 76,000 (as determined by GPC/LALLS) sold by SWS Silicones, Inc.
[4]including cyclomethicone contained in silicone gum premix; see note 2, above
[5]mixture of 87% isobutane and 13% propane (by weight of total propellant)

An aerosol antiperspirant is made by putting the antiperspirant active into an aerosol can. The silicone gum, amino-functional silicone, cyclomethicone and fragence are premixed, and added to the can. The propellant is then added, under pressure, and the can sealed.

The aerosol antiperspirant, as formulated above, is applied to the underarm of a human subject, reducing the perspiration in the applied area.

EXAMPLE II

An aerosol antiperspirant composition of the present invention is made comprising:

| Component | % by weight |
|---|---|
| aluminum chlorhydrate | 9.000 |
| silicone gum | 0.440 |
| SWS 801 amino-functional silicone | 0.750 |
| cyclomethicone | 2.655 |
| ethylene brassyate | 0.005 |
| isobutane propellant | 87.150 |

The silicone gum and the cyclomethicone are mixed. The antiperspirant active is put in an aerosol can, and the amino-functional silicone material and the silicone gum/cyclomethicone mixture then added. The propellant is added and the can sealed.

EXAMPLE III

An antiperspirant composition of the present invention is made, comprising:

| Component | % by weight |
|---|---|
| ZAG active[1] | 10.00 |
| Petrarch 2181[2] | 4.90 |
| propane propellant | 85.10 |

[1] zironium-aluminum-glycine hydroxychloride complex antiperspirant active
[2] monoamino-functional silicone, of molecular weight of approximately 134,000 (as determined by CPC/LALLS), sold by Petrarch System, Inc.

EXAMPLE IV

An antiperspirant composition of the present invention was made comprising:

| Component | % by weight |
|---|---|
| Westwood DM200 ACH[1] | 9.00 |
| SE32 Silicone gum[2] | 2.61 |
| GE 176-10979[3] | 0.01 |
| cycomethicone (D-5) | 1.03 |
| perfume | 0.20 |
| propellant A-46 | 87.15 |

[1] 5/6 aluminum chlorhydrate antiperspirant active, sold by Westwood Chemical Company
[2] high molecular weight silicone gum, with a viscosity of approximately $4.5 \times 10^6$ centipoise, sold by General Electric Company
[3] diamino-functional silicone, of molecular weight of approximately 19,000 (as determined by GPC), sold by Geneal Electric Company The silicone gum, cyclomethicone and amino-functional silicone were mixed. The antiperspirant active was put into an aerosol container, and the silicone mix was then added after mixing with the fragrance. The propellant was then added, under pressure, and the can sealed.

The aerosol antiperspirant, as formulated above, is applied to the underarm area of a human subject, reducing perspiration in the applied area.

EXAMPLE V

An antiperspirant composition of the present invention is made comprising:

| Component | % by weight |
|---|---|
| Westwood DM200 ACH | 12.00 |
| SE Silicone gum | 1.89 |
| GE 176-10979 | 0.01 |
| cyclomethicone (D-5) | 1.75 |
| perfume | 0.20 |
| propellant A-46 | 84.15 |

An antiperspirant aerosol, comprised as above, is made in a manner similar to that described in Example IV.

EXAMPLE VI

An antiperspirant composition, according to the present invention, was made comprising:

| Component | % by weight |
|---|---|
| Reheis 501 ACH | 9.00 |
| PS402 Carboxy-functonal siloxane* | 0.44 |
| propellant A-46 | 90.56 |

*functional siloxane sold by Petrarch Systems, Inc.

An antiperspirant aerosol was made in a manner similar to that described in Example IV. An antiperspirant composition was also made comprised as above, but substituting PS183 fluoro-functional silicone, sold by Petrarch Systems, Inc., with substantially-similar results.

What is claimed is:

1. An antiperspirant aerosol composition, comprising:
   (a) from about 1% to about 40% of aparticulate antiperspirant material;
   (b) from about 0.005% to about 6.0% of functionalized siloxane having the formula $$X_a-R-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_b----\left[\underset{\underset{\underset{X}{|}}{\overset{R^1}{|}}}{\overset{\overset{CH_3}{|}}{Si}}O\right]_c----\underset{\underset{CH_3}{|}}{\overset{\overset{CH_3}{|}}{Si}}-R-X_a$$

wherein a is 0 or 1, b is from about 50 to about 2000, and c is from about 0 to about 300; X is selected from the group consisting of Cl, F, —COOH, and —N(R$^3$)$_2$; R is CH$_3$ (if a=0) or R$^1$ (if a=1); R$^1$ is straight or branched alkyl containing from 1 to 10 carbon atoms; R$^2$ is selected from the group consisting of H and R$^1$; R$^3$ is selected from the group consisting of R$^2$ and R$^1$N(R$^2$)$_2$; and wherein a+C>0 and the ratio of (a+c)/(b+c) is from about 0.01 to about 0.3; and
   (c) from about 60% to about 95% of an aerosol propellant.

2. An antiperspirant aerosol composition, according to claim 1, wherein in said functionalized siloxane X is —N(R$^3$)$_2$.

3. An antiperspirant composition according to claim 2, wherein said amino-functional siloxane is diamine substituted.

4. An antiperspirant aerosol composition according to claim 3, wherein said amino-functional siloxane material has a molecular weight of from about 20,000 to about 150,000.

5. An antiperspirant aerosol composition, according to claim 4, wherein said amino-functional siloxane material is present at a level of from about 0.005% to about 2.0%.

6. An antiperspirant aerosol composition, according to claim 1, wherein said particulate antiperspirant material is present at a level of from about 5% to about 12%.

7. An antiperspirant aerosol composition, according to claim 1, additionally comprising from about 0.05% to about 5.0% of a silicone gum material selected from nonfunctionalized siloxanes having a viscosity of from about 500,000 to about 100,000,000 centistokes at 25° C.

8. An antiperspirant aerosol composition, according to claim 7, wherein said silicone gum is present at a level of from about 0.1% to about 2.0%.

9. An antiperspirant aerosol composition, according to claim 7, additionally comprising from about 0.05% to about 15.0% of a volatile silicone oil.

10. An antiperspirant aerosol composition, consisting essentially of:
(a) from about 1% to about 40% of a particulate antiperspirant material;
(b) from about 0.005% to about 6.0% of a functionalized siloxane having the formula

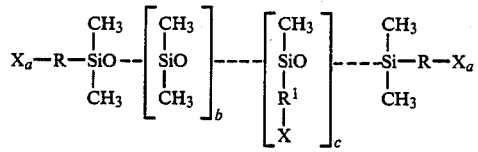

wherein a is 0 or 1, b is from about 50 to about 2000, and c is from about 0 to about 300; X is selected from the group consisting of Cl, F, —COOH, and —N(R$^3$)$_2$; R is CH$_3$ (is a=0) or R$^1$ (if a =1); R$^1$ is straight or branched alkyl containing from 1 to 10 carbon atoms; R$^2$ is selected from the group consisting of H and R$^1$; R$^3$ is selected from the group consisting of R$^2$ and R$^1$N(R$^2$)$_2$; and wherein a+c>0 and the ratio of (a+c)/(b+c) is from about 0.01 to about 0.3; and
(c) from about 0.05% to about 5.0% of a silicone gum material selected from nonfunctionalized siloxanes having a viscosity of from about 500,000 to about 100,000,000 centistokes at 25° C.;
(d) from about 0.05% to about 15.0% of a volatile silicone oil; and
(e) from about 60% to about 95% of an aerosol propellant.

11. An antiperspirant composition, according to claim 10, wherein in said functionalized siloxane X is —N(R$^3$)$_2$.

12. An antiperspirant aerosol composition, according to claim 11, wherein said amino-functional siloxane material is diamine substituted.

13. An antiperspirant aerosol composition according to claim 10, wherein said amino-functional siloxane material has a molecular weight of from about 20,000 to bout 150,000.

14. An antiperspirant aerosol composition, consisting essentially of:
(a) from about 5% to about 12% of a particulate antiperspirant material;
(b) from about 0.005% to about 0.1% of an amino-functional siloxane having the formula:

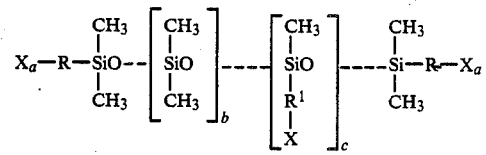

wherein a is 0 or 1, b is from about 50 to about 2000, and c is from about 0 to about 300; X is —N(R$^3$)$_2$; R is ACH$_3$ (if a=0) or R$^1$ (if a=1); R$^1$ is straight or branched alkyl containing from 1 to 10 carbon atoms; R$^2$ is selected from the group consisting of H and R$^1$; R$^3$ is selected from the group consisting of R$^2$ and R$^1$N(R$^2$)$_2$; and wherein a+c>0 and the ratio of (a+c)/(b+c) is from about 0.01 to about 0.3; and
(c) from about 0.1% to about 20% of a silicone gum material selected from nonfunctionalized siloxanes having a viscostiy of from about 500,000 to about 100,000,000 centistokes at 25° C.; and
(d) from about 0.05% to about 15% of a volatile silicone oil;
(e) from about 0.001% to about 0.5% of a perfume; and
(f) from about 60% to about 95% of an aerosol propellant.

* * * * *

UNITED STATES PATENT AND TRADEMARK OFFICE
CERTIFICATE OF CORRECTION

PATENT NO. : 4,806,338
DATED : February 21, 1989
INVENTOR(S) : Scott E. Smith

It is certified that error appears in the above-identified patent and that said Letters Patent is hereby corrected as shown below:

In column 9, line 18 "is a = 0" should read -- if a = 0 --.

In column 10, line 21 "$ACH_3$" should read -- $CH_3$ --.

Signed and Sealed this

Third Day of July, 1990

Attest:

HARRY F. MANBECK, JR.

*Attesting Officer*   *Commissioner of Patents and Trademarks*